(12) United States Patent
Dey et al.

(10) Patent No.: US 11,879,898 B2
(45) Date of Patent: Jan. 23, 2024

(54) METHOD FOR MEASURING TESTOSTERONE USING LC-MSMS

(71) Applicant: DH Technologies Development Pte. Ltd., Singapore (SG)

(72) Inventors: Subhakar N Dey, Lexington, MA (US); Michal Weinstock, Framingham, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 253 days.

(21) Appl. No.: 17/417,572

(22) PCT Filed: Dec. 23, 2019

(86) PCT No.: PCT/IB2019/061305
§ 371 (c)(1),
(2) Date: Jun. 23, 2021

(87) PCT Pub. No.: WO2020/129032
PCT Pub. Date: Jun. 25, 2020

(65) Prior Publication Data
US 2022/0057412 A1 Feb. 24, 2022

Related U.S. Application Data

(60) Provisional application No. 62/783,657, filed on Dec. 21, 2018.

(51) Int. Cl.
*G01N 33/00* (2006.01)
*G01N 33/74* (2006.01)
(Continued)

(52) U.S. Cl.
CPC .......... *G01N 33/743* (2013.01); *G01N 1/34* (2013.01); *G01N 1/4077* (2013.01); *G01N 30/04* (2013.01);
(Continued)

(58) Field of Classification Search
CPC .................................................... G01N 33/743
(Continued)

(56) References Cited

PUBLICATIONS

Yesildal et al. "A practical ID-LC-MS/MS method for the most commonly analyzed steroid hormones in clinical laboratories" Turk J Biochem 2019; 44(2): 130-141; published online Aug. 21, 2018 (Year: 2018).*

(Continued)

*Primary Examiner* — Christine T Mui
*Assistant Examiner* — Emily R. Berkeley (57) ABSTRACT

The teachings herein provide for a method of analyzing testosterone using mass spectrometry. The method entails combining in a vial or well, a tagging reagent that is reactive with testosterone, an aqueous precipitation agent that precipitate proteins from solution, and an internal standard solution, the internal standard solution containing a known concentration of an isotopically enriched testosterone and then adding to the vial or well, a sample containing or suspected to contain testosterone. The vial can then be mixed to cause simultaneous precipitation of proteins and reaction of any testosterone present with the tagging reagent to form a mixture of a precipitate and a liquid solution. The liquid solution can then be separated from any precipitate and then analyzed for testosterone using liquid chromatography tandem mass spectrometry.

14 Claims, 10 Drawing Sheets

(51) Int. Cl.
*G01N 1/34* (2006.01)
*G01N 1/40* (2006.01)
*G01N 30/04* (2006.01)
*G01N 30/72* (2006.01)
*G01N 30/02* (2006.01)
*G01N 30/06* (2006.01)

(52) U.S. Cl.
CPC ..... *G01N 30/72* (2013.01); *G01N 2001/4083* (2013.01); *G01N 2001/4088* (2013.01); *G01N 2030/027* (2013.01); *G01N 2030/045* (2013.01); *G01N 2030/067* (2013.01); *G01N 2560/00* (2013.01)

(58) Field of Classification Search
USPC .......................................................... 436/173
See application file for complete search history.

(56) References Cited

PUBLICATIONS

International Search Report and Written Opinion for PCT/IB2019/061305 dated Apr. 24, 2020.

M Star-Weinstock et al: "LC-ESI-MS/MS Analysis of Testosterone at Sub-Picogram Levels Using a Novel Derivatization Reagent", Analytical Chemistry, vol. 84, Sep. 20, 2012, pp. 9310-9317. XP055078161.

U Bussy et al: "Chemical derivatization of neurosteroids for their trace determination in sea lamprey by UPLC-MS/MS", Talanta, vol. 149, Nov. 26, 2015 pp. 326-334. XP029366898.

N Nadarajah et al: "Multiplexed analysis of steroid hormones in saliva by LC-MS/MS with 2-hydrazinopyridine derivatization", Clinical Mass Spectrometry, vol. 4-5, Apr. 1, 2017 pp. 1-10. XP055681952.

C Polson et al: "Optimization of protein precipitation based upon effectiveness of protein removal and ionization effect in liquid chromatography-tandem mass spectrometry", Journal of Chromatography B, vol. 785, No. 2, Mar. 5, 2003, pp. 263-275. XP027121063.

M Star-Weinstock et al: "Development of a CDC-certified total testosterone assay for adult and pediatric samples using LC-MS/MS", Clinical Mass Spectrometry, vol. 13, May 27, 2019, pp. 27-35, XP055681843.

\* cited by examiner

METHOD FOR MEASURING TESTOSTERONE USING LC-MSMS

RELATED APPLICATION

This application claims the benefit of priority from U.S. Provisional Application No. 62/783,657, filed on Dec. 21, 2018, the entire contents of which is incorporated by reference herein.

FIELD

The present teachings generally relate to methods for mass spectrometer analysis of testosterone.

INTRODUCTION

Clinical diagnostics lab assays should be simple, cost-effective, quick, and robust. In addition, alignment of the assay results (bias and imprecision) to a gold standard, such as the CDC reference method (Clinical Chemistry, Vol. 59(2), pp. 372-380, incorporated by reference herein), has important implications for patient health. The increasing trend is to draw as little blood as possible from a patient, especially from pediatric and neonatal populations, thus dictating assays to meet the sensitivity and accuracy requirements for both small sample size and the lowest reference level of the desired analyte in a population. In young adult females, testosterone levels are more than 15-fold lower than the levels in young adult males (2-45 ng/dL and 250-1100 ng/dL, respectively). In pediatric samples, total testosterone levels are the lowest in females and males aged 2-10 years and can be <20 ng/dL. As children reach puberty, the levels increase significantly until adulthood, but during tanner stage I the levels can be ≤5 ng/dL. In children, measurement of testosterone is important for identifying cases of inborn errors of sex steroid metabolism and delayed or precocious puberty. In adult females and males, low testosterone levels lead to infertility, sexual dysfunction, fatigue, loss of muscle mass, and mood swings. The diagnosis of androgen deficiency in males and females, as well as the assessment of testosterone levels in pediatric samples, requires a highly specific, accurate, and sensitive measurement procedure.

Small to medium-sized hospital labs analyzing relatively low sample volumes (<100/day) could benefit from a highly sensitive method utilizing manual sample preparation, which is easy for beginner level operators. Simple and economical automated sample preparation with rapid analysis would be desirable for large or core clinical laboratories analyzing high sample volumes.

Though a previous testosterone analysis publication (Analytical Chemistry, Vol. 84(21), pp. 9310-7, incorporated by reference herein) was aimed to describe an ultra-high sensitivity method designed to enhance sensitivity for the quantification of free testosterone, dried blood spots, female, and/or pediatric serum samples, the method presented here is aimed to enhance simplicity and robustness.

SUMMARY

The present method provides a simple, robust, and sensitive solution for all laboratories performing low level testosterone analysis. Analyte extraction and derivatization are performed simultaneously.

In various embodiments, a method for analyzing total testosterone in a sample is disclosed which comprises the steps of: a) combining a tagging reagent that is reactive with testosterone, an aqueous precipitation agent that precipitate proteins from solution, and an internal standard solution, the internal standard solution containing a known concentration of an isotopically enriched testosterone, and a sample containing or suspected to contain testosterone, b) mixing the combination to cause simultaneous precipitation of proteins and reaction of any testosterone present with the tagging reagent to form a mixture of a precipitate and a reacted liquid solution, c) separating the precipitate from the reacted liquid solution, e) analyzing the reacted liquid solution using tandem mass spectrometry to identify and/or quantitate the sample testosterone. In some aspects, the reacted liquid solution may be processed using liquid chromatography prior to introduction into the tandem mass spectrometer.

In some embodiments, the tagging reagent comprises a compound of formula:

In some embodiments, the aqueous precipitation agent comprises zinc sulfate.

In some embodiments, the separating the precipitate in the mixture comprises filtering the mixture through a filter medium contained in a filter plate and collecting the liquid solution as a filtrate in a collection plate.

In various embodiments, a method for analyzing total testosterone in a sample is described which comprises the steps of: a) combining in a microcentrifuge vial, a compound of formula:

an aqueous solution containing zinc sulfate, and a solution containing 2,3,4,-$^{13}C_3$-testosterone, b) adding to the microcentrifuge vial, a serum or plasma sample containing or suspected to contain testosterone, c) mixing the vial, d) centrifuging the vial, e) separating a supernatant in the vial from any precipitate, f) analyzing the supernatant using tandem mass spectrometry for testosterone. In some aspects, processing the supernatant using liquid chromatography (LC column) and eluting resulting separated supernatant from the LC column to the mass spectrometer for analysis.

In various embodiments, a method for analyzing total testosterone in a sample is described which comprises the steps of: a) combining in a well of a filter plate, a compound of formula:

an aqueous solution containing zinc sulfate, and a solution containing 2,3,4,-$^{13}C_3$-testosterone, b) adding to the well, a calibrator, control, or patient sample containing or suspected to contain testosterone, c) shaking the filter plate to cause mixing, d) filtering contents from the well in the filter plate into a collection plate by use of centrifuging to form a filtrate in the collection plate, e) analyzing the filtrate using tandem mass spectrometry for testosterone.

In some embodiments of the above, the analyzing comprises measuring MRM transitions of 403.3/164.2 or 403.3/152.2 in a tandem mass spectrometer.

In some embodiments of the above, the analyzing comprises measuring MRM transitions of 406.3/167.2 or 406.3/155.2 in a tandem mass spectrometer, and wherein the isotopically enriched testosterone is 2,3,4 $^{13}C_3$-testosterone.

In various embodiments, a kit comprising a combination of a tagging reagent with at least one of an aqueous solution of a precipitation solution and an isotopically enriched testosterone. In some aspects, wherein the precipitation solution comprises zinc sulfate. In some aspects, the tagging reagent comprises a compound of formula:

DETAILED DESCRIPTION OF EMBODIMENTS

An accurate and robust total testosterone ESI-LC-MS/MS quantification method with simple sample preparation workflow and sufficient sensitivity for serum or plasma samples of all gender and age groups, via ketone functional group derivatization (using for example, AMPLIFEX™ Keto Reagent) was created. The method for analyzing total testosterone in a sample comprises the steps of: creating a sample solution by combining: a tagging reagent reactive with testosterone such as AMPLIFEX™ Keto reagent, an aqueous precipitation agent that precipitates proteins from solution, and an internal standard solution containing a known concentration of an isotopically enriched testosterone. A sample containing or suspected to contain sample testosterone may be added to the combination for testing and analysis. The resulting sample solution is then mixed to precipitate proteins and react any testosterone present with the tagging reagent to form a mixture of a precipitate and a reacted liquid solution. The precipitate is then separated from the reacted liquid solution, for instance by centrifugation. Other known means of separation may also be employed, for instance by manipulating magnetic beads to capture the precipitated protein. The separated and reacted liquid solution may also commonly be referred to as the supernatant. The reacted liquid solution, i.e. supernatant, may then be injected into a tandem mass spectrometer to identify and/or quantitate the sample testosterone if present in the sample. Depending upon requirements, and as known in the art, a liquid chromatograph column (LC column) may be employed to filter, concentrate and separate compounds in the reacted liquid solution before introduction into the tandem mass spectrometer. Alternative means for processing the reacted liquid solution may also be employed in place of the LC column and the processed sample may be then be introduced into the mass spectrometer using flow-injection analysis (FIA) or infusion using a syringe pump as known in the art.

A simple sample preparation method to accommodate low and high sample volumes was developed using simultaneous protein precipitation and derivatization with a mass tagging reagent such as AMPLIFEX™ Keto reagent to create a mixture of a precipitate and a reacted liquid solution. In some embodiments, the mixture may then be processed by centrifugation to separate the precipitate from the reacted liquid to create a separated supernatant. In some embodiments, the supernatant may then be injected into a liquid chromatograph (LC) tandem mass spectrometry (MS/MS) system (SCIEX TOPAZ™ IVD LC-MS/MS, in which MS is equivalent in performance to a SCIEX 4500 MD) for analysis to detect and/or quantitate testosterone.

The specific equipment and sequence of steps recited below are by way of example and a skilled person in the art will understand that equivalent known processing steps may be substituted from the specific examples and equipment recited below.

In example experiments, total testosterone in human serum or plasma samples was quantified using an external calibration curve generated by calibrators spanning a broad concentration range of ~1-2000 ng/dL (10-20,000 pg/mL), traceable to NIST 971 SRM. $^{13}C_3$-enriched testosterone internal standard was added in a constant amount to calibration standards and unknown samples to correct for analyte loss during samples preparation or matrix effect during analysis. Two methods, one using a 96 well filter plate and another using Eppendorf tubes, were developed. Both methods were certified by the Centers for Disease Control (CDC) hormone standardization program for Testosterone (HoSt T). The feasibility of implementing the method for plasma and serum samples was tested via a small scale method comparison study between matched pediatric serum and plasma samples derived from the same donor. In addition, plasma samples collected in two different anticoagulant tube types (Li-heparin and K2EDTA) were compared to samples originating from the same donor.

AMPLIFEX™ Keto reagent

Using in-house formulated NIST 971-traceable calibrators, the method was linear (r2>0.999) between 1 to 2000 ng/dL (10 and 20,000 pg/mL) with a limit of detection of approximately 1 ng/dL (10 pg/mL). The testosterone concentration bias against 40 reference samples from CDC HoSt T standardization program was <3% with an average % CV of ~4. More than 80% of samples passed the CDC bias criteria of ±6.4%. Comparison between pediatric matched serum and plasma samples resulted in high correlation (r2=0.997) and bias of <5%. The difference between matched adult serum and plasma samples was ~1%.

Feasibility for an accurate and streamlined method suitable for measuring total testosterone in all human samples was demonstrated with a choice of sample preparation workflow to suit low or high number of samples. The method can potentially be used for plasma matrix from different blood collection tubes (Li-Heparin and K2EDTA).

The method presented here enables quantification of total testosterone from human serum (or plasma) using a small sample size of 100 μL with a lower limit of quantitation (LLOQ) of approximately 1 ng/dL (10 pg/mL). The teachings herein describe two variations of the sample preparation workflow to accommodate small or large clinical lab requirements. The first workflow involves manual operation by which testosterone extraction is performed in an individual tube. It is designed for a smaller sample load (<100/day). The second workflow uses 96-well filter plates on an automated sample preparation platform that can also be used with manual pipetting should an automated pipetting platform not be available. Both the individual tube and 96-well filter plate methods have been certified by the CDC HoSt T standardization program.

Certified standard solutions of testosterone (100 m/mL in acetonitrile, 99.8% pure), 2,3,4-$^{13}C_3$-testosterone (10 μg/mL in acetonitrile, 99.8%), and epi-testosterone (1 mg/mL in acetonitrile, 99.7% pure) were purchased from Cerilliant (Round Rock, Tex.). A system suitability solution (SST) was prepared in-house from the above testosterone, epi-testosterone and 2,3,4 $^{13}C_3$ testosterone in MeOH/H$_2$O 1/1 (V/V). ZnSO$_4$·7H$_2$O was purchased from Sigma Aldrich and prepared as a 0.4 M solution with ultra-pure water (18 MΩ Elga LabWater system, USA). No further pH adjustment was necessary. Methanol, acetonitrile and formic acid, mass spectrometry grade solvents were purchased from VWR International (Radnor, Pa.). Bovine serum albumin (BSA, part number A2153) was purchased from Sigma Aldrich (St. Louis, Mo.) as lyophilized powder. Testosterone Standard Reference Material (SRM) NIST 971 was purchased from National Institute of Standards and Technology (Gaithersburg, Md.). One or more of the components above may be incorporated into a kit.

CDC serum samples were analyzed as part of the HoSt T Hormone Standardization program (CDC Atlanta, GA). Pediatric plasma (lithium heparin (LH), K2EDTA)/serum matched samples were purchased from iSpecimen (Lexington, MA). The AMPLIFEX™ Keto Reagent kit was obtained from SCIEX (Framingham, MA). The contents of the reagent vial and the diluent vial were mixed 1:1 (V/V) prior to use to obtain the final AMPLIFEX™ Keto Reagent solution. Details of the derivatization procedures, chemistry, and geometric isomer formation upon derivatization are described in Analytical Chemistry, Vol. 84, pp. 9310-7, incorporated by reference herein.

For sample extraction, microcentrifuge tubes, 96-well filter plates, 96 well collection plates, as well as the filter plate covers were obtained from SCIEX. The LC autosampler tubes and snap caps were purchased from VWR International.

Calibrators and controls were prepared in-house using 5% BSA as matrix, which was determined to be free of endogenous testosterone by our assay. Testosterone working stock solution was prepared from the certified standard solution of testosterone (100 μg/mL in acetonitrile, Cerilliant). This working solution was used to spike into the 5% BSA solution to make the highest concentration calibrator of 2000 ng/dL (~20,000 pg/mL). The highest concentration calibrator was further diluted with 5% BSA to prepare the other calibrator concentrations (1.8, 8, 16, 59.9, 144.7, 844.2, and 1842.6 ng/dL) and quality control levels (4, 32.7, and 476.8 ng/dL). The concentrations of the calibrators and controls are traceable to NIST 971, Standard Reference Material (SRM) of testosterone in human serum matrix.

System Suitability (SST) Solution

A SST was used to monitor the performance of the LC-MS/MS system before analyzing calibrators and unknown samples and was prepared as follows. A mixture of testosterone, 2,3,4-13C3-testosterone, and epi-testosterone (10, 5, and 3 μg, respectively) was derivatized with 1000 μL of final AMPLIFEX™ keto reagent solution for 120 minutes at ambient temperature in a microcentrifuge vial. The derivatized solution was transferred to a 100 mL volumetric flask and the volume was filled up to 100 mL using 1:1 (V/V) methanol-water, resulting in a stock solution of 0.1, 0.05, and 0.03 μg/mL in testosterone, 2,3,4-13C3-testosterone, and epi-testosterone, respectively. This stock solution was further diluted 500-fold using 1:1 (V/V) methanol-water to obtain the final SST: testosterone, 200 pg/mL (20 ng/dL); 2,3,4-13C3-testosterone, 100 pg/mL (10 ng/dL); and epi-testosterone, 60 pg/mL (6 ng/dL). The SST was stored at −20° C.

Internal Standard (IS) Solution

To correct for any variability in sample preparation and analysis, a methanol solution of 2,3,4-$^{13}C_3$-testosterone (20 ng/mL, prepared by diluting the 10 μg/mL certified standard) was used as an IS. This solution was spiked into each sample, calibrator, or control before sample preparation.

Figure 1:
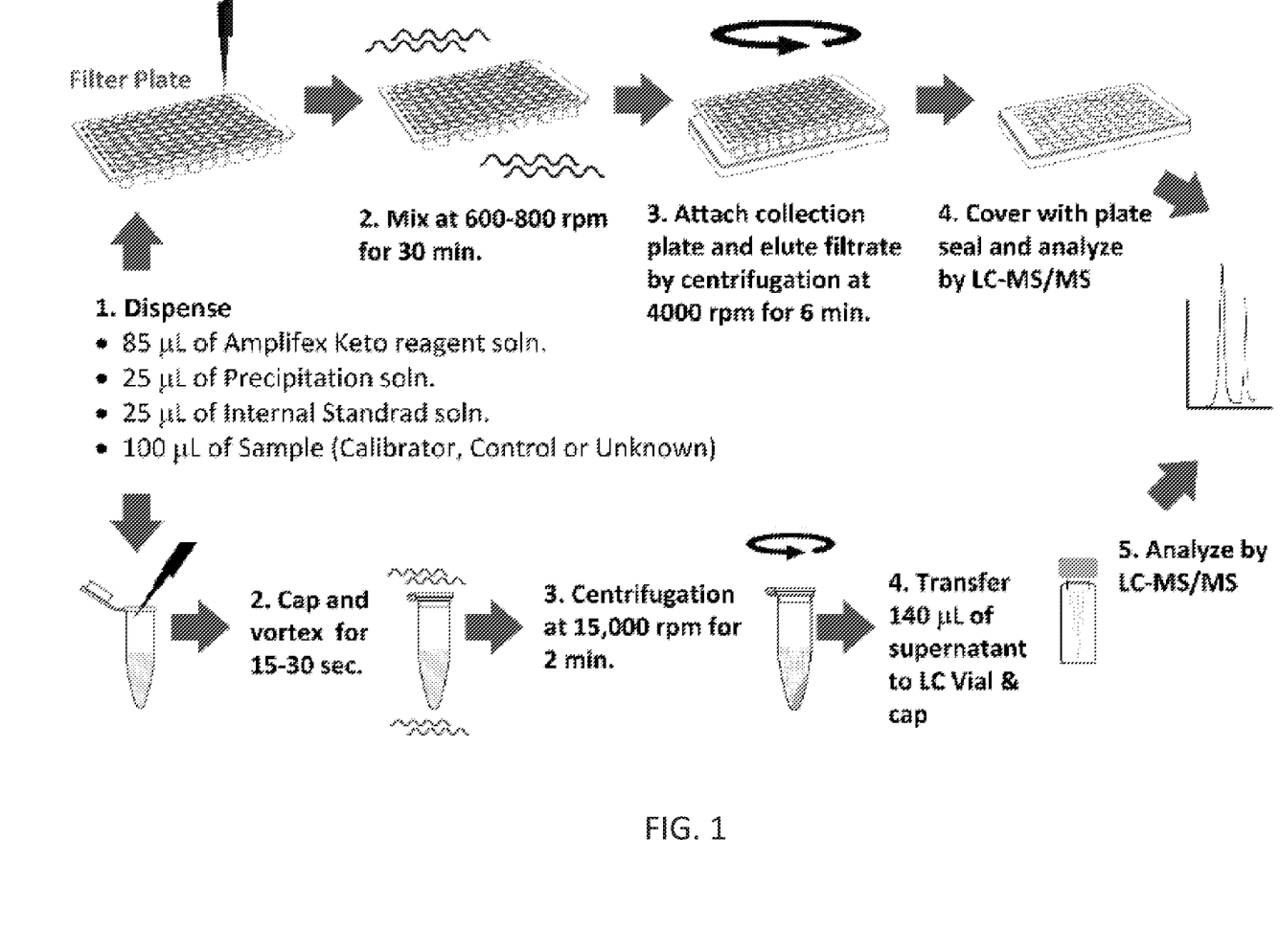
FIG. 1 depicts an exemplary sample preparation workflow that accommodates both single tube and 96-well plate methods.

FIG. 1 demonstrates exemplary embodiments of the sample preparation using either individual sample tubes (or vials) or a 96-well filter plate. The use of a 96-well filter plate allows for easy automation and high volume testing.

When using a 1.5 mL microcentrifuge vial to prepare a sample, 85 μL final AMPLIFEX™ keto reagent solution, 25 μL precipitation solution (containing the precipitation agent, zinc sulfate (ZnSO$_4$) 0.4 M), and 25 μL IS solution were added to the vial. 100 μL of serum or plasma sample, calibrator, or control was then transferred to each individually labeled microcentrifuge vial. After vortex mixing for 15-30 seconds, the protein precipitated sample was incubated for 30 minutes at room temperature and centrifuged for 2 minutes at 15,000 rpm to separate precipitated protein from the reacted liquid solution. A total of 140 μL of the supernatant, i.e. reacted liquid solution, was then separated and transferred to an autosampler vial (polypropylene with 300 μL insert) for LC/MS/MS analysis.

When utilizing a 96-well plate sample preparation, the following sample preparation steps can be performed with either manual pipetting or an automated robotic platform. The automated sample preparation was performed partially on a TOPAZ™ Prep Station (SCIEX, Framingham, MA) platform using a 96-well filter plate stacked on top of a collection plate. The following order of reagents was dispensed manually onto the filter plate: 85 μL of AMPLIFEX™ Keto reagent solution, 25 µL precipitation solution containing a precipitation agent, 25 µL of IS solution, and 100 µL of calibrators, controls, or patient samples. Next, the non-covered filter plates were loaded onto specific racks of the prep station and the collection plate on a separate rack. An assay-specific programmed script was initiated for the robot to perform plate shaking at 600 rpm for 30 min at ambient temperature (20-30° C.) and centrifugation of 4000 rpm for 4 minutes (The robotic arm attaches the filter plate and the collection plate inside the integrated centrifuge). The collection plate (with the collected filtrate) was covered with an adhesive seal and placed in the autosampler of the LC/MS/MS system for analysis.

If an automated platform is not available, shaking and centrifugation of the filter plate can be performed on any standard 96-well plate shaker, such as the Eppendorf Thermomixer R, and a centrifuge with plate rotors, such as the Eppendorf 5430 with A-2-MTP rotor.

The incubation time during derivatization could also aid in improving the protein precipitation and testosterone extraction efficiency, as it is common practice to incubate the samples upon extraction.

LC-MS/MS Method

Figure 2:
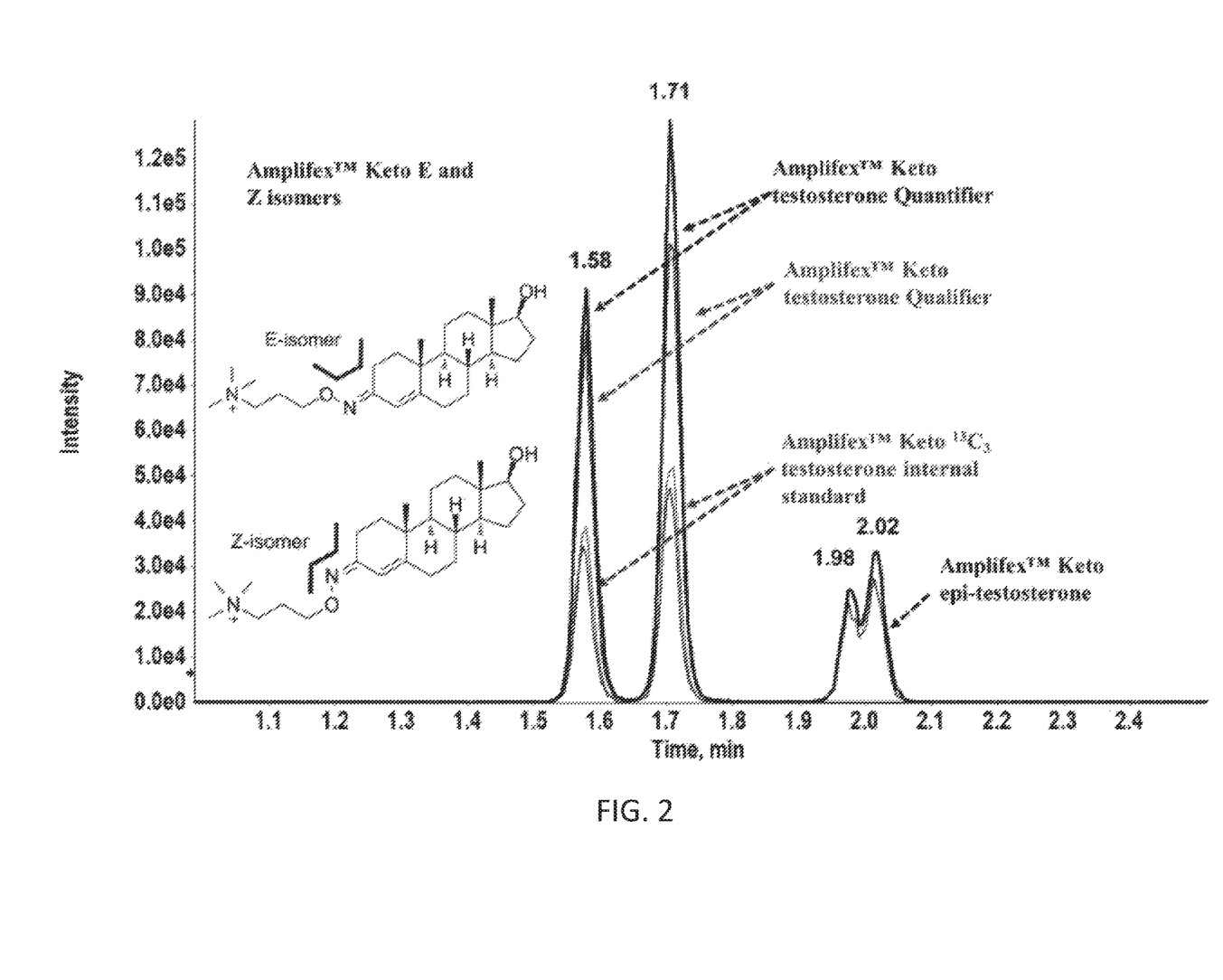
FIG. 2 depicts a chromatogram of derivatized testosterone, epi-testosterone and $^{13}C_3$ testosterone internal standard.

Prepared samples (prepared either by individual vials or in 96-well filter plate method) were analyzed on the TOPAZ™ IVD LC-MS/MS System (SCIEX 4500MD LC-MS/MS). The SST containing derivatized testosterone, epi-testosterone, and internal standard $^{13}C_3$-testosterone, was injected in triplicate prior to analysis to qualify the LC/MS/MS system performance producing the chromatogram depicted in FIG. 2. Injection volume was 50 µL for each unknown sample, calibrator, control and SST. The LC gradient allowed for baseline separation of the geometric isomers (E and Z isomers) of AMPLIFEX™ keto-testosterone formed after derivatization. The geometric isomers (E-Z) of AMPLIFEX™ Keto-testosterone oximes are separated as double peaks. The HPLC mobile phases were 0.1% formic acid in water (Mobile Phase A) and 0.1% formic acid in acetonitrile (Mobile Phase B). A Phenomenex Kinetex biphenyl column (50×3.0 mm, 5 µm) was used at 40° C. with a gradient profile as shown in Table 1 for analytical separation. The diverter valve on the mass spectrometer was used to bypass the excess reagent elution and LC column wash. The LC run time is shorter than those utilized in the past, and a more robust analytical column is used with larger diameter and particle size to better suit the analytical lab requirements.

TABLE 1

LC gradient profile

| Time (Minutes) | Mobile Phase B (Percentage) | Flow Rate (ml/min) | Diverter Valve Switching Program |
|---|---|---|---|
| 0 | 10 | 0.8 | 1.0 min diversion from waste to LC column |
| 0.5 | 30 | 0.8 | To MS (analysis) |
| 2.5 | 38 | 0.8 | |
| 2.6 | 95 | 0.8 | |
| 2.7 | 95 | 1.2 | At 3.0 min from LC column to waste |
| 3.1 | 95 | 1.2 | |
| 3.2 | 10 | 0.8 | |
| 3.7 | 10 | 0.8 | |

The MS/MS fragments used as quantifier and qualifier MRM transitions were 403.3→164.2 and 403.3→152.2, respectively. The transitions for the derivatized $^{13}C_3$-testosterone IS quantifier and qualifier were 406.3→167.2 and 406.3→155.2, respectively. The declustering potential (DP) was 80V, collision energy (CE) 57 eV, ion spray energy 3000 V, and the cell exit potential (DP) 5V. The source temperature was set to 650° C. and curtain gas (CUR) to 25 psi.

Unknown sample concentrations were calculated based on the calibration curve generated with the calibrators described above. The concentration versus the ratio between AMPLIFEX™ Keto-testosterone (analyte) and AMPLIFEX™ Keto-13C3-testosterone (IS) was used for the linear regression analysis. Geometric isomer peaks were integrated and added for both the analyte and the IS. SCIEX ANALYST® MD 1.6.2 and MultiQuant MD 3.0.2 programs were used for LC-MS/MS method optimization, data acquisition, data processing and quantification. The acceptable accuracy from the assigned value for the calibrators and controls was ±15%, except from the lowest calibrator, for which acceptable accuracy was ±20%.

The Lower Limit of Quantitation (LLOQ) was estimated after serial dilutions of NIST 971 female reference sample of 27.7 ng/dL (in triplicates) to the following concentrations: 6.93, 2.77, 1.39, 0.69 and 0.34 ng/dL with 5% BSA as diluent. The LLOQ criteria were % CV≤15 (n=3) and a signal-to-noise (S/N) ratio≥10. In addition, the S/N ratio was evaluated for the lowest calibrator level on four different days and the concentration for which the S/N ratio would equal 10 was estimated. Method interference studies are described in detail in ref (12).

The CDC certification process is described in detail on the CDC website under "Laboratory Quality Assurance and Standardization Programs" (Laboratory Quality Assurance and Standardization Programs. Centers for Disease Control and Prevention. September 2018., incorporated by reference herein). Assay certification by the CDC hormone standardization program for testosterone (HoSt T) was obtained for both sample preparation methods, the individual vials and the 96 well filter plate. First, the method was calibrated with 40 HoSt T Phase 1 samples and two NIST 971 SRMs. The reference concentrations of these 42 samples were compared to those determined by our method using Pearson correlation and percent bias calculation. Once the method passed the CDC acceptable bias criteria of ±6.4%, we enrolled in Phase 2 of the HoSt T certification program in which 10 blindfolded samples were shipped to our lab for analysis every 3 months (Q1 through Q4). Our calculated concentrations were reported back to the CDC for cumulative bias and imprecision estimation (bias estimation by CDC was based on CLSI guidelines EP9-A2 "Method comparison and bias estimation using patient samples"). The acceptable imprecision is <5.3%, and was calculated as the average % CV of all 40 samples (n=4 for each sample). The Phase 2 program is renewed every four quarters. The data provided here are from the first certification cycle. Method correlation (Pearson) and percent difference plots were generated using the Analyse-it software package and Excel 2016.

Using the individual vial sample preparation method, we compared the calculated concentrations for serum and plasma obtained from the same individual's blood draw (matched samples). Two separate studies were conducted. In one study we compared matched samples from adult donors (9 female and 8 male) aged 21-65 years. Each donor's blood collection was divided into three different tubes: (i) serum, (ii) plasma lithium heparin (LH), and (iii) plasma K2EDTA. In this study, we compared not only the calculated concentrations between serum and plasma, but also between different common plasma anticoagulation tubes. In the other study we compared matched serum and plasma LH samples from 20 presumably healthy pediatric donors (10 female and 10 male) aged 7-18 years from mixed ethnicity and race.

Figure 3A:
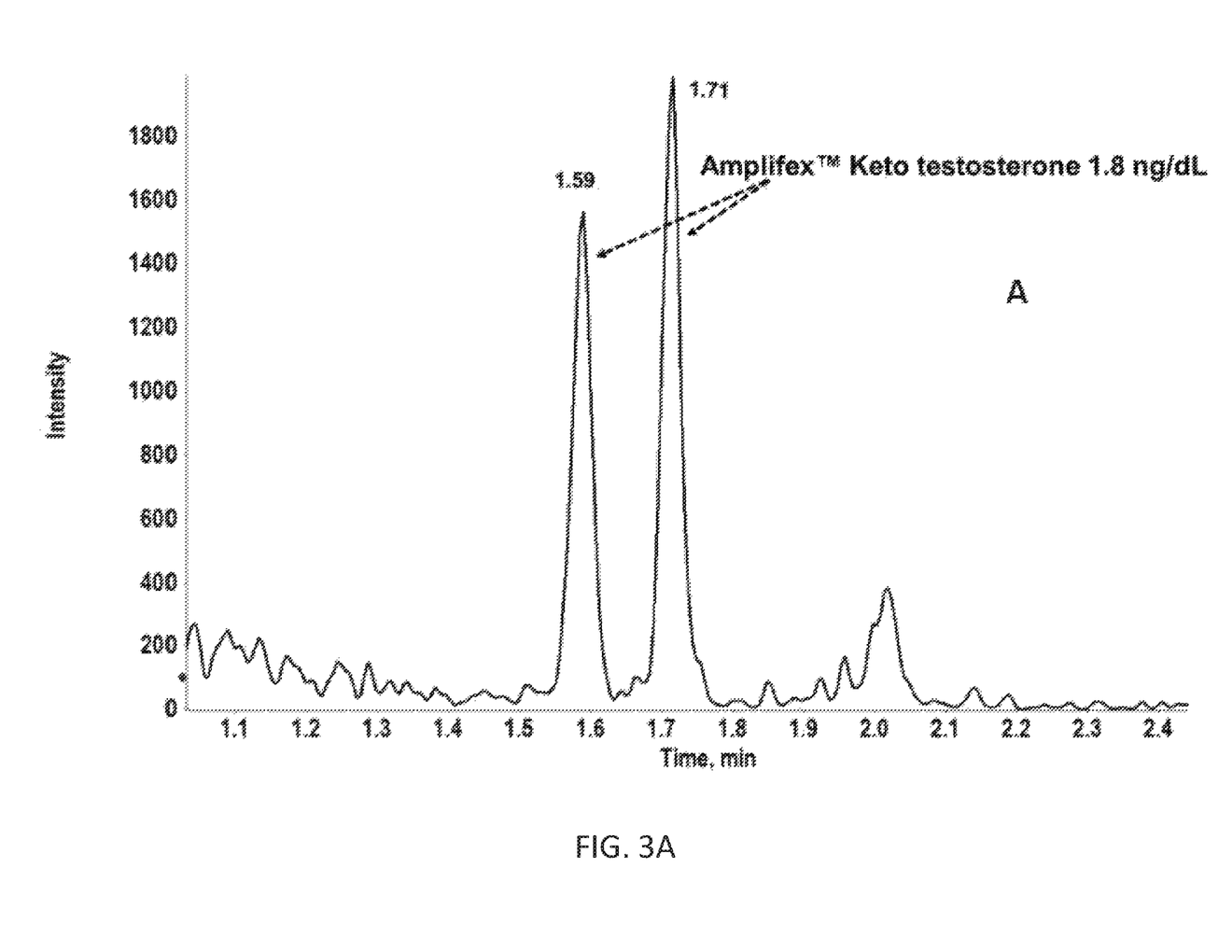
FIG. 3A depicts a chromatogram of a calibrator.
Figure 3B:
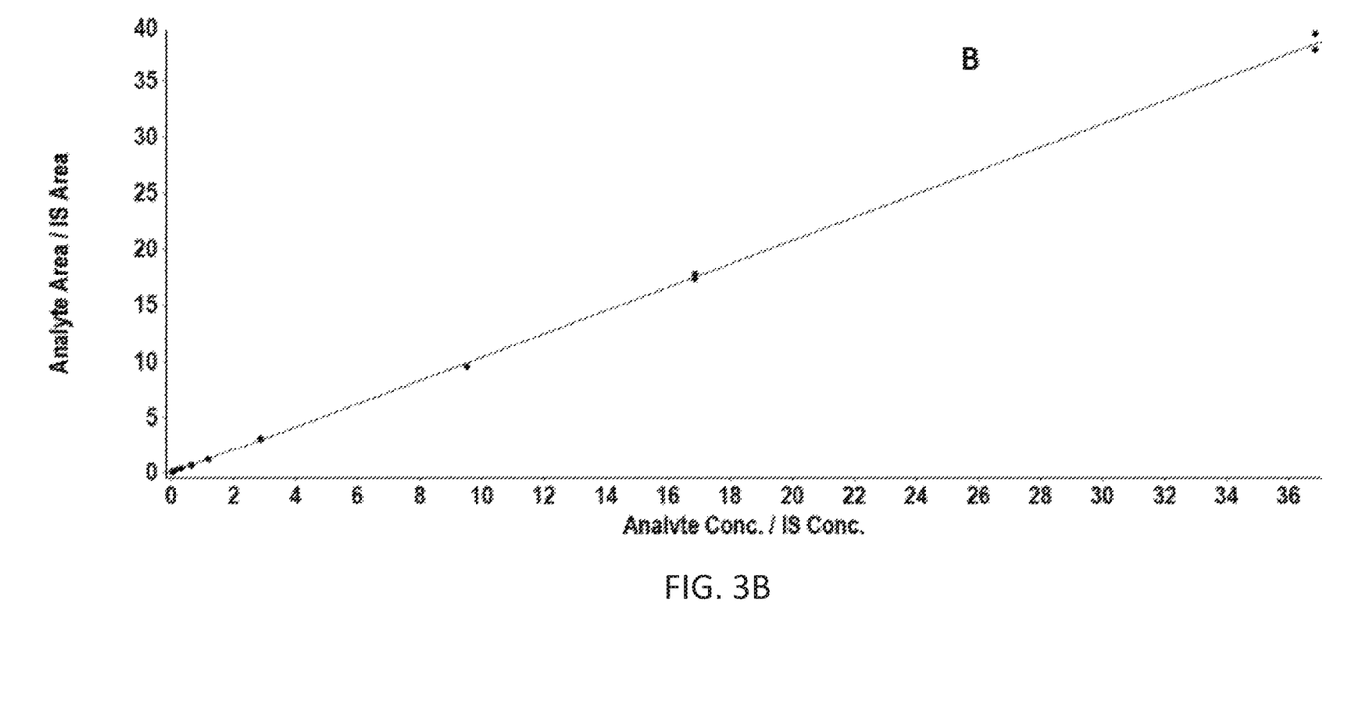
FIG. 3B depicts a calibration curve

FIG. 3A depicts a representative chromatogram of our lowest calibrator of 1.8 ng/dL (18 pg/mL) AMPLIFEX™ Keto testosterone. Based on repeated serial dilutions of NIST 971 female sample and from the SN ratio of the lowest calibrator level over different days, the LLOQ was estimated to be 1 ng/dL (10 pg/mL). The LLOQ is adequate for measuring testosterone in serum and plasma samples from female and pediatric sources for the vast majority of clinical purposes. The averaged % CV of each calibrator level over four different days ranged from 5.1 (lowest calibrator) to 2.8 (highest calibrator). This simple sample preparation procedure involving simultaneous protein precipitation, analyte derivatization and extraction (without the need to dry and re-constitute the samples) is linear between 1 and 2000 ng/dL (10-20,000 pg/mL) with $r^2>0.99$ after 1/x weighting which is depicted in the calibration curve of FIG. 3B. This calibration curve comprises six concentration levels, 1.8-1843 ng/dL. The equation of the straight line was $y=1.04+0.00146$ ($r=0.9998$).

Figure 4:
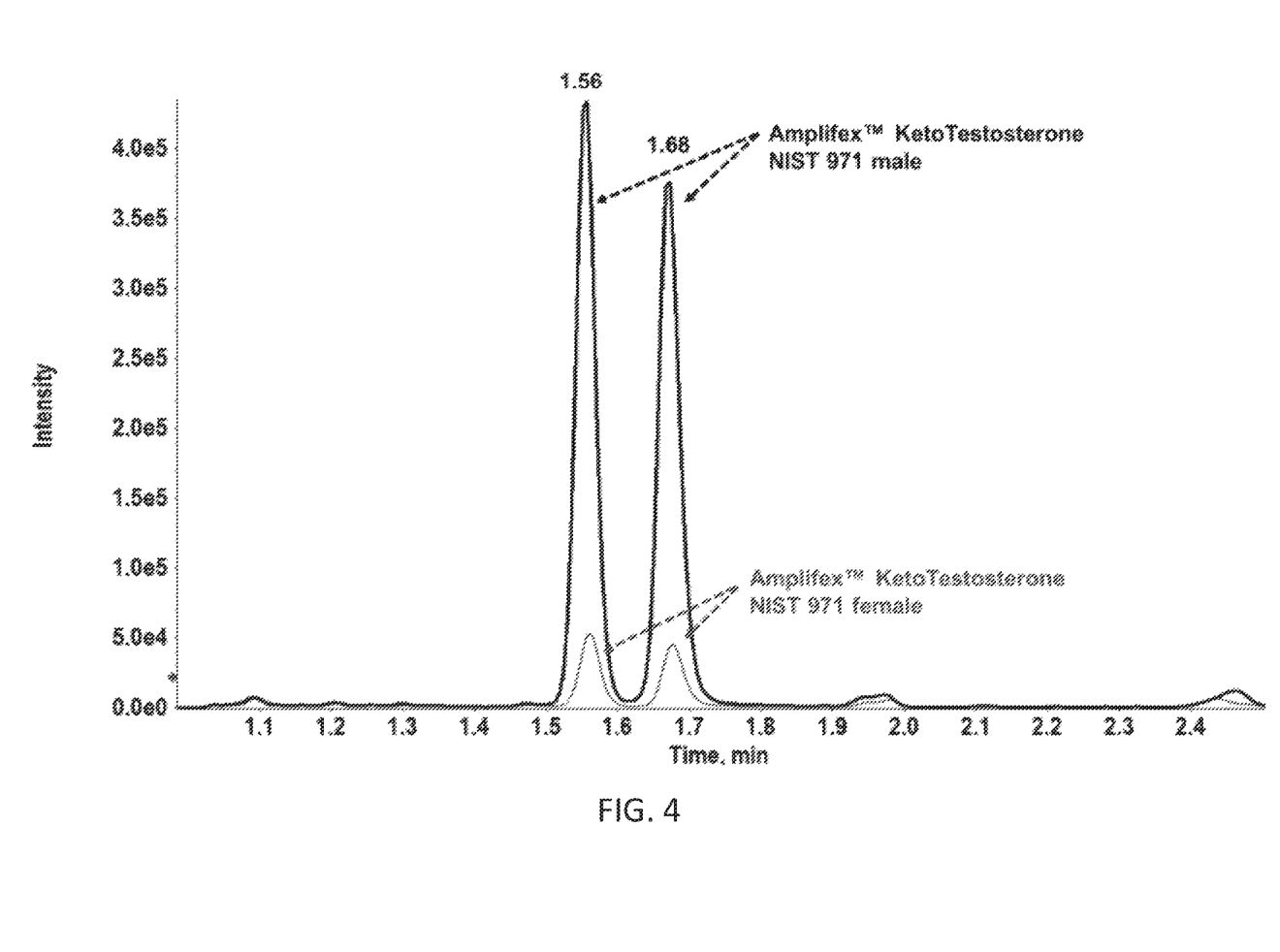
FIG. 4 depicts an overlaid chromatogram of male and female NIST reference standards.

The calibrators and quality controls were traceable to NIST SRM 971. On each day of analysis, two concentration levels of NIST 971 were added as an extra quality control from a different source. FIG. 4 shows a representative overlaid chromatogram of male and female NIST 971, in which testosterone concentrations are 643.5 ng/dL and 27.72 ng/dL, respectively (values obtained from the Certificate of Analysis of NIST 971.

Figure 5:
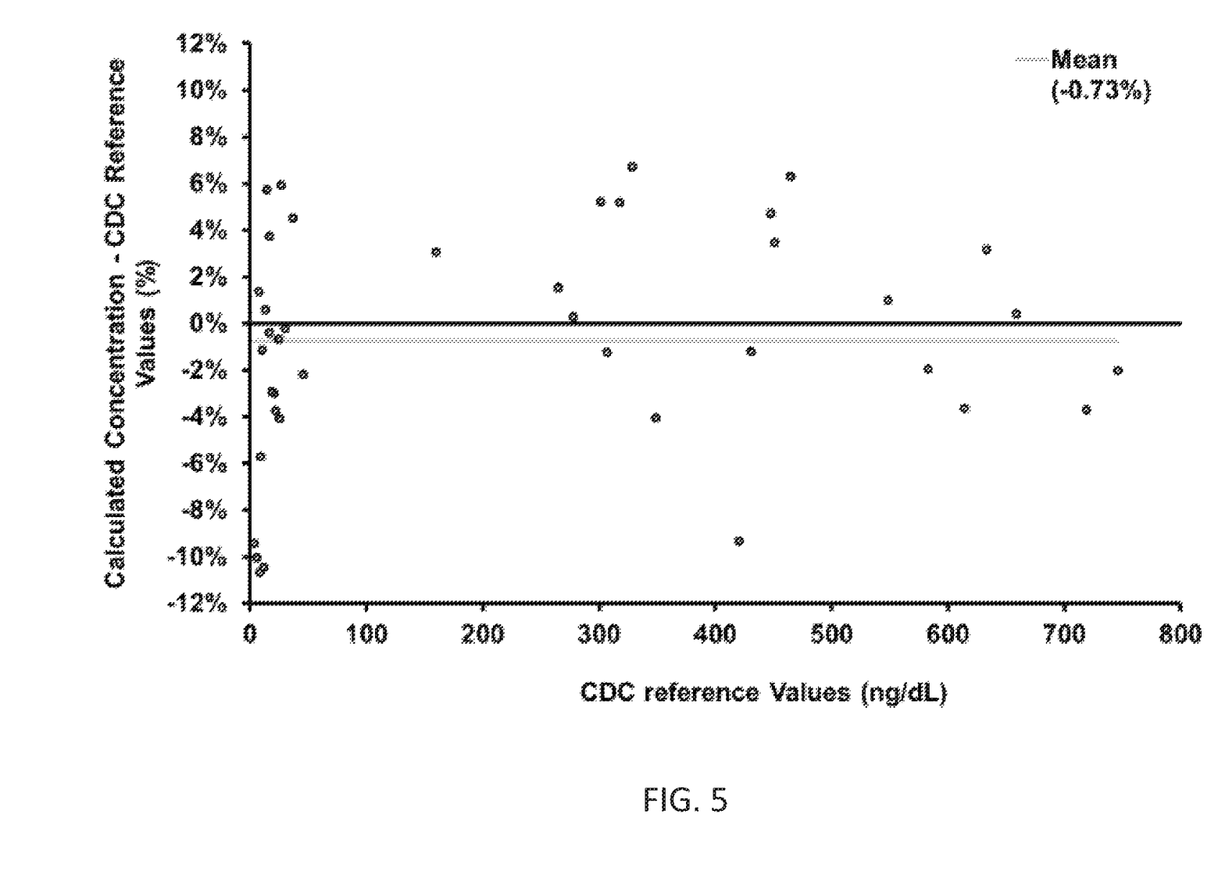
FIG. 5 depicts a mean difference plot between the reference and the calculated testosterone concentrations of 40 serum samples from CDC Hormone Standardization program. (HoSt T).

The first step in the process of method of HoSt T certification with CDC standardization was to pass the acceptable criteria for the 40 value-assigned serum samples from HoSt T Phase 1, which is a bias of ±6.4%. Comparing the method utilized with the within teachings, to the CDC reference method (Mean Difference plot depicted in FIG. 5), the mean bias over the measurement range (1.8-1843 ng/dL) was −0.73% and the correlation coefficient (Pearson evaluation) r was 0.999 (FIG. 6), indicating high correlation and agreement with CDC reference concentrations, which enabled us to proceed to Phase 2 of the HoSt T program). FIG. 5 shows a comparison of the methods between the CDC reference and the procedure in accordance with the present teachings using 40 Phase 1 HoSt T serum samples. The lower line of the Mean Difference plot represents the mean bias.

Figure 6:
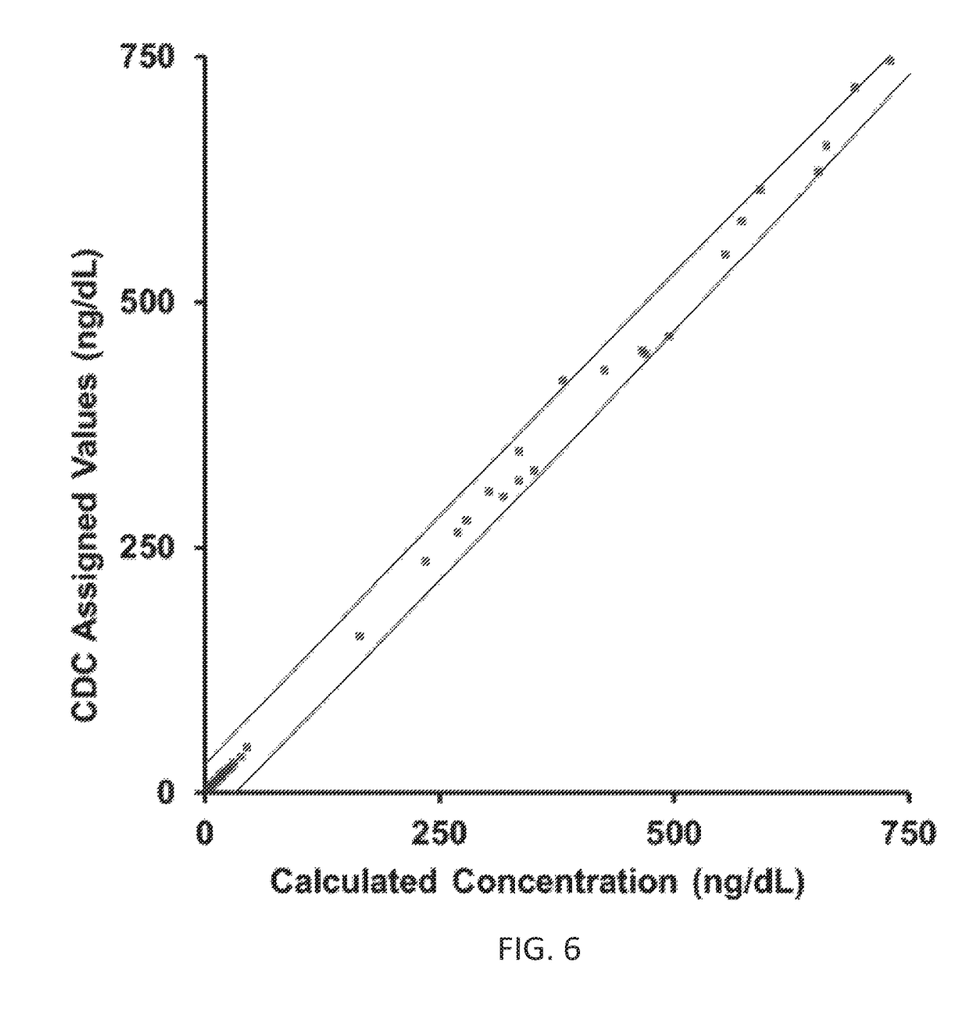
FIG. 6 depicts a Pearson correlation between the reference and the calculated testosterone concentrations of 40 serum samples from CDC HoSt T program.

FIG. 6 depicts a Pearson correlation between HoSt T Phase 1 reference samples concentrations and the calculated concentrations (ng/dL) using the present teachings. Correlation coefficient r=0.999. The lines define the 95% Confidence Interval.

A summary of method performance results, including a comparison with the CDC method is given in Table 2. The average bias (% difference) of <3% between the measured concentrations using the present teachings and the CDC reference concentrations is far below the acceptable ±6.4%. In addition, the proportion of samples meeting CDC bias criteria (Certified Total Testosterone Procedures. September 2018. being >80% is another indication of high method accuracy. The reproducibility expressed as the averaged % CV of all samples seems to be comparable between the individual vial and plate methods, was 3.68% and 3.94% respectively. The % CV of only female samples was slightly higher than that of male samples due to a much lower testosterone concentration range, but remained within the acceptable value of ≤5.3%, in both sample preparation methods.

Figure 7A:
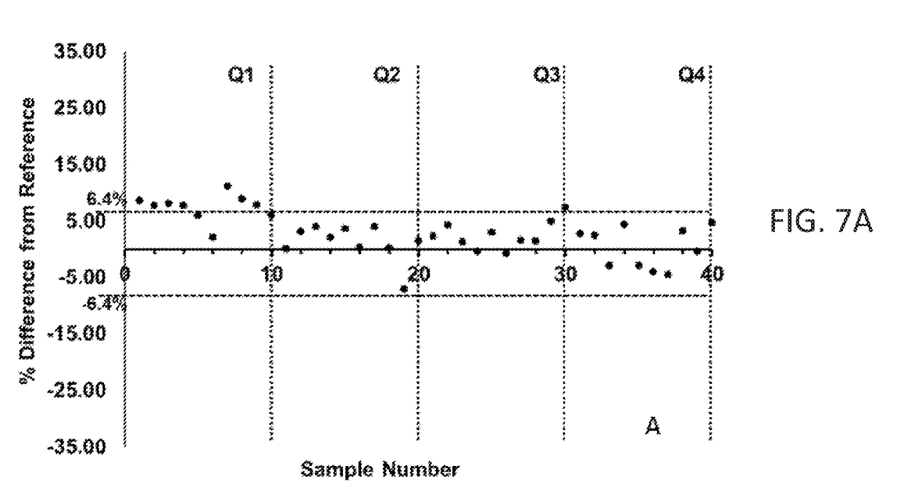
FIGS. 7A and 7B depict the percent difference between the CDC reference value and the determined mean value over a period of one year.
Figure 7B:
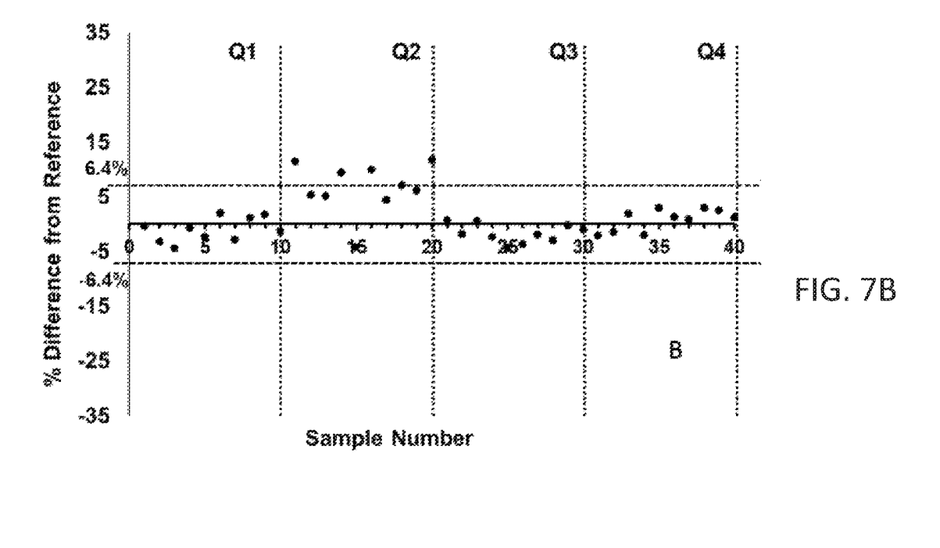

FIGS. 7 A and B illustrate the individual sample bias throughout the cycle year for each of the sample preparation methods. Overall, individual sample concentrations were very close to the reference value, however for each of the methods there was one quarter in which the bias with CDC reference concentrations was higher than in the rest of the year. In particular, FIGS. 7A and 7B depict the percent difference between the CDC reference value and the determined mean value utilizing the present teachings throughout the cycle year. FIG. 7A shows the analysis utilizing the individual tube/vial sample preparation and FIG. 7B shows the 96-well filter plate automated method.

TABLE 2

Method performance after the first cycle year of Phase 2 HoSt T standardization.

| | Characteristic | Tube Method (Manual) | Plate Method (Automated) |
|---|---|---|---|
| Method | LLOQ (ng/dL) | 1.0 | 1.0 |
| | Dynamic Range (ng/dL) | 1.0-2000 | 1-2000 |
| CDC Certification Report | % Bias against CDC Reference Method | Average: −1.2 Min: −11.6 Max: 4.4 | Average: −2.9 Min: −11.2 Max: 7.1 |
| | 95% Confidence Interval of Mean % Bias | −2.6 to 0.2 | −4.2 to 1.6 |
| | Pearson Correlation Coefficient (r) | 0.999 | 0.999 |
| | Proportion of samples Meeting Bias Criteria (%) | 88 | 78 |
| | % CV Female (n = 20,) | 3.68 (5.2-45.8 ng/dL) | 5.2 (7.3 to 45.8 ng/dL) |
| | % CV Male (n = 20,) | 2.4 (160 to 746 ng/dL) | 2.7 (160 to 821 ng/dL) |

Figure 8:
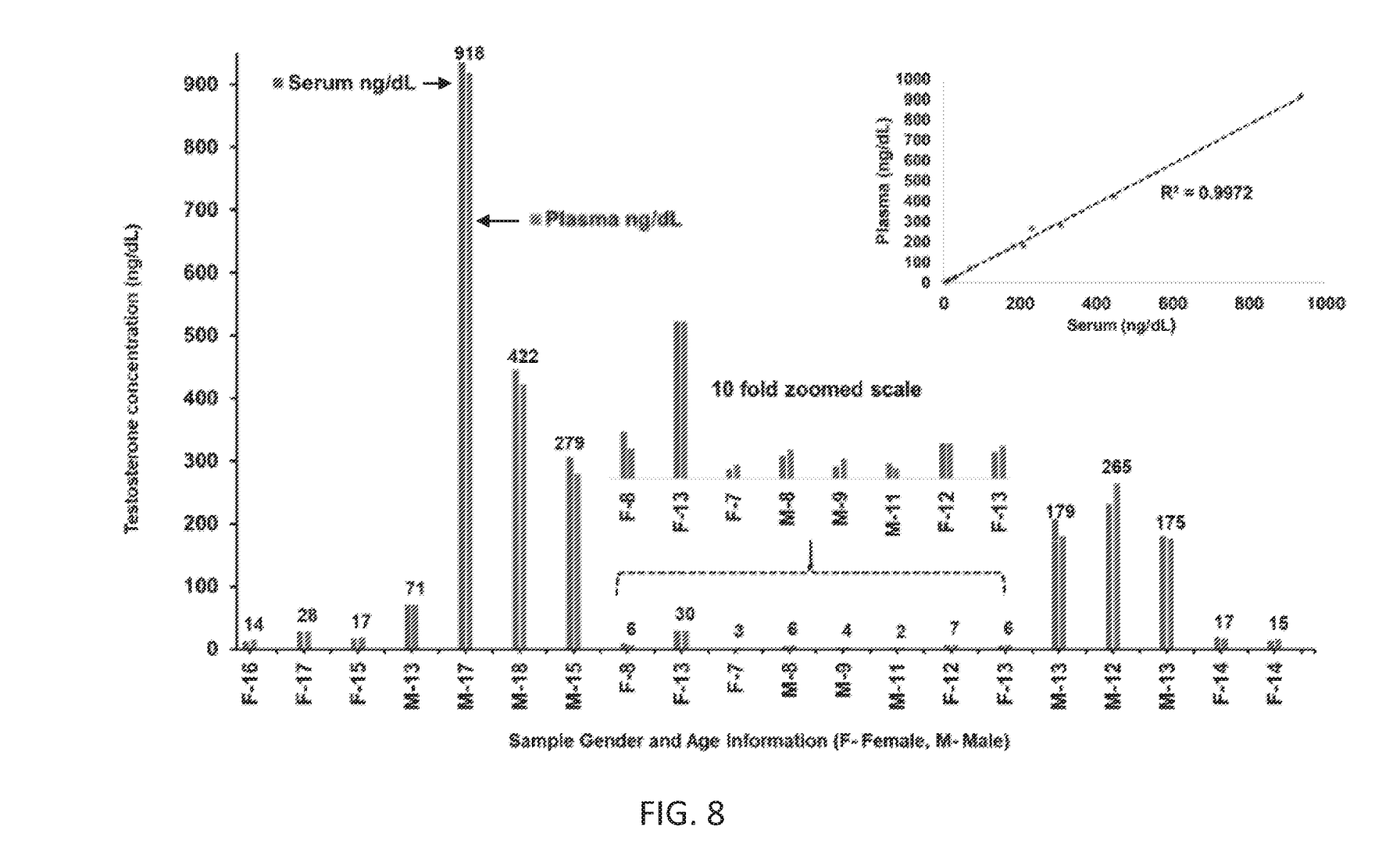
FIG. 8 depicts the calculated testosterone concentrations of 20 matched serum/plasma pediatric samples and the corresponding correlation plot.

The CDC does not offer parallel certification program for plasma samples. It was also determined whether the present teachings showed the ability to reliably measure testosterone in plasma samples and to test whether a difference exists between anticoagulants in plasma collection tubes. As plasma samples include fibrinogen and therefore have higher protein content, the concentration of an analyte in serum and plasma may differ depending on the analyte (Clinical Chemistry, Vol. 50, pp. 1704-1705, *Differences between Human Plasma and Serum Metabolite Profiles*. Zhonghao, Y., et al. 7, 2011, FLOS One, Vol. 6, both incorporated by reference herein) As a preliminary evaluation, 37 samples were measured for testosterone in matched serum/plasma samples from both genders and a broad age range in two experiments. FIG. 8 depicts results of an analysis of 20 pediatric samples aged 7-18 years which indicated high correlation between endogenous serum and plasma concentrations. The measured testosterone concentrations were 1.7-934 ng/dL, and the average bias was <5%, indicating no clinically significant difference in testosterone concentration between serum and plasma samples. The measured concentrations of the plasma samples are shown on the top of the bar chart in FIG. 8.

Figure 9:
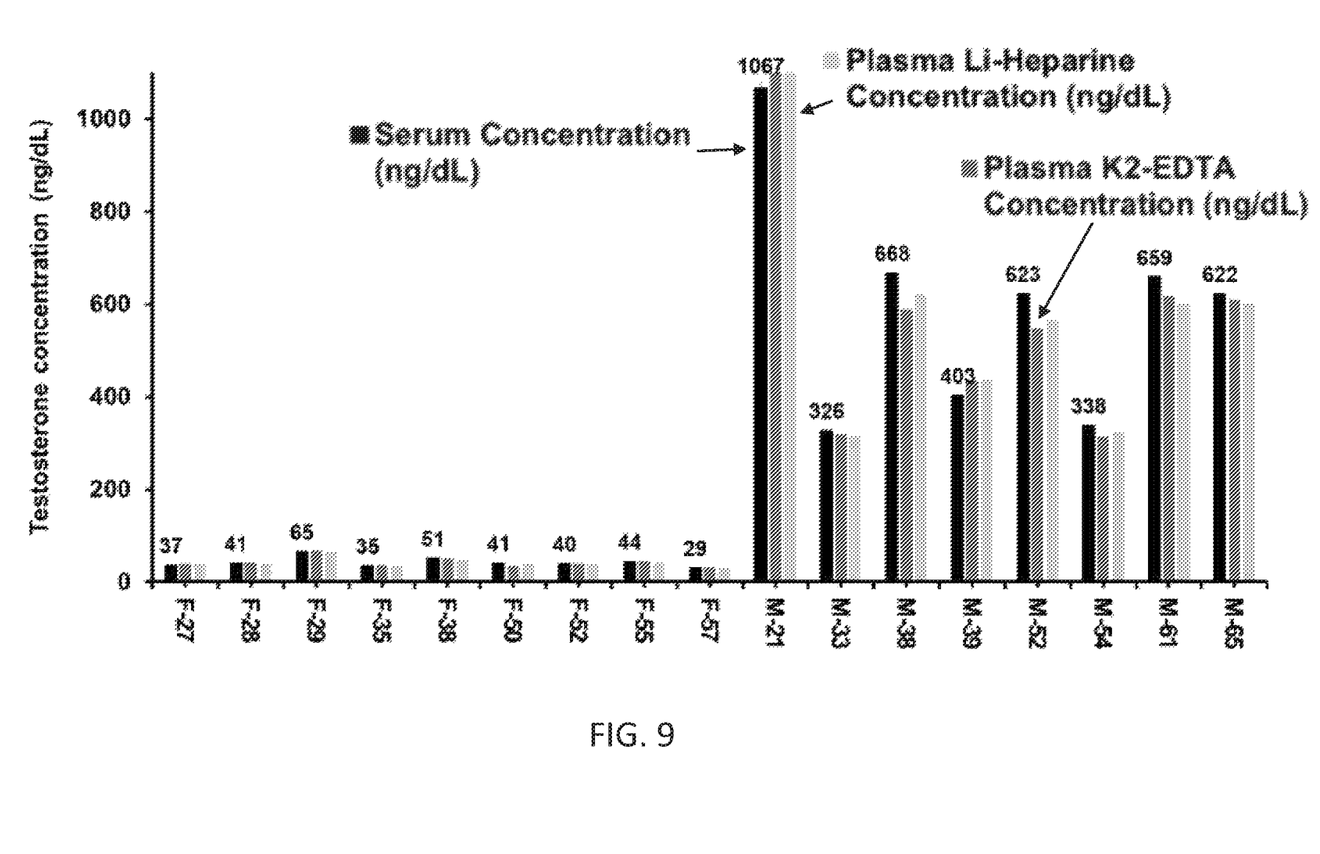
FIG. 9 depicts the testosterone concentrations calculated for 17 adult matched serum/plasma (two types).

Similarly, the analysis of 17 matched adult samples of serum versus plasma LH or plasma K2EDTA resulted in comparable testosterone concentrations. For each of the 17 samples the % CV among serum, plasma LH, and plasma K2EDTA, was ≤8 (n=3), with an overall average of 4% (n=51, 3 matched samples for each of the 17 donors, each was measured once). These results are shown in FIG. 9 which shows the testosterone concentrations calculated for 17 matched adult samples, in particular, serum, plasma Li-heparin, and plasma K2EDTA. In the X axis of FIG. 9, the sample name includes information on gender and age (e.g. F-27 originated from female, age 27 years). The displayed concentrations in the bar chart are from the serum calculated concentrations.

In addition, looking at the percent difference among the three samples from each individual donor, the average between serum and plasma, or between plasma LH and plasma K2EDTA was ~1%, ranging from 0.04 to 11.6%.

Twenty pediatric serum samples, aged 2-15 years, mixed genders and race (not plasma matched) were analyzed. The calculated testosterone concentrations ranged from 0.9 to 662 ng/dL. The lowest concentration was calculated for a 2-year-old male and the highest for a 13-year-old male.

Our goal was to develop an accurate, specific, sensitive, and robust sample preparation and LC-MS/MS method to measure testosterone in a broad range of sample concentrations, including female and pediatric sources and various sample types. Our first published LC/MS/MS method for analyzing testosterone from serum (12) was intended for -ultra-high sensitivity (≤0.1 ng/dL) as it involved a separate derivatization step and a larger sample volume. The sample preparation for the method described here attempted to reduce time, extraction solvent, sample volume, and cost. We also eliminated the need for special sample drying equipment. The enhanced sensitivity is enabled by derivatization to attach a charged moiety to carbon 3 of testosterone using a tagging reagent, such as AMPLIFEX™ Keto Reagent.

However, unlike other methods that involve a separate derivatization step, in this method the derivatization reagent solution containing a mass tagging reagent is used simultaneously for protein precipitation in one simple analyte extraction step. This method can be performed easily on an automated robotic platform with a 96-well filter plate attached to a collection plate. Both workflows, the individual vials and the 96-well filter plate (PrepStation robot), were successfully certified by the CDC HoSt T program with a very high accuracy score. Both methods are suitable for quantifying testosterone samples on a SCIEX TOPAZ™ IVD LC-MS/MS System (4500MD) within a broad dynamic range of approximately 1-2000 ng/dL (10-20,000 pg/mL). Thus, the method demonstrated sufficient sensitivity and accuracy that is required to reduce the need to repeat samples due to ambiguous results and assure measurement consistency across different laboratories. The method can be used to analyze plasma samples with either LH or K2EDTA as anticoagulant, but for plasma samples there would be a need to evaluate a larger number of matched serum/plasma samples from various anticoagulant tubes (>40, or as recommended in the Clinical and Laboratory Standard Institute guidelines) (CLSI EP9-A2. Measurement Procedure Comparison and Bias Estimation Using Patient Samples, Vol. 22. 19) In addition, it would be necessary to confirm serum/plasma concentration equivalency with the 96-well filter plate workflow.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method for analyzing total testosterone in a sample comprising the steps:
   creating a sample solution by combining:
   a tagging reagent reactive with testosterone,
   an aqueous precipitation agent that precipitates proteins from solution,
   an internal standard solution containing a known concentration of an isotopically enriched testosterone, and
   a sample containing or suspected to contain sample testosterone,
   mixing the sample solution to precipitate proteins and react any testosterone present with the tagging reagent to form a mixture of a precipitate and a reacted liquid solution,
   separating the precipitate from the reacted liquid solution,
   analyzing the reacted liquid solution using tandem mass spectrometry to identify and/or quantitate the sample testosterone.

2. The method of claim 1, wherein before the analyzing using tandem mass spectrometry the method further comprises:
   introducing the reacted liquid solution into a liquid chromatography column to separate compounds in the reacted liquid solution, and
   eluting the separated reacted liquid solution to the tandem mass spectrometer for analysis.

3. The method of claim 1 wherein the tagging reagent comprises a compound of formula:

4. The method of claim 1 wherein the aqueous precipitation agent comprises zinc sulfate.

5. The method of claim 1 wherein the separating the precipitate comprises filtering the mixture through a filter medium contained in a filter plate and collecting the reacted liquid solution as a filtrate in a collection plate.

6. The method of claim 1 wherein the analyzing comprises measuring MRM transitions of 403.3/164.2 or 403.3/152.2.

7. The method of claim 1 wherein the analyzing comprises measuring MRM transitions of 406.3/167.2 or 406.3/155.2, and wherein the isotopically enriched testosterone comprises 2,3,4 $^{13}C_3$-testosterone.

8. A method for analyzing total testosterone in a sample comprising the steps of:
   a) combining in a microcentrifuge vial, a compound of formula:

an aqueous solution containing zinc sulfate, and a solution containing 2,3,4,-$^{13}C_3$-testosterone,
b) adding to the microcentrifuge vial, a serum or plasma sample containing or suspected to contain testosterone,
c) mixing the microcentrifuge vial,
d) centrifuging the microcentrifuge vial,
e) separating a supernatant in the microcentrifuge vial from any precipitate,
f) analyzing the supernatant using tandem mass spectrometry for testosterone.

9. The method of claim 8 wherein the analyzing comprises measuring MRM transitions of 403.3/164.2 or 403.3/152.2.

10. The method of claim 8 wherein the analyzing comprises measuring MRM transitions of 406.3/167.2 or 406.3/155.2.

11. A method for analyzing total testosterone in a sample comprising the steps of:
a) combining in a well of a filter plate, a compound of formula:

an aqueous solution containing zinc sulfate, and a solution containing 2,3,4,-$^{13}C_3$-testosterone,
b) adding to the well, a calibrator, control, or patient sample containing or suspected to contain testosterone,
c) shaking the filter plate to cause mixing,
d) filtering contents from the well in the filter plate into a collection plate by use of centrifuging to form a filtrate in the collection plate,
e) analyzing the filtrate using tandem mass spectrometry for testosterone.

12. The method of claim 11 wherein the analyzing comprises measuring MRM transitions of 403.3/164.2 or 403.3/152.2.

13. The method of claim 11 wherein the analyzing comprises measuring the MRM transitions of 406.3/167.2 or 406.3/155.2.

14. The method of claim 11 wherein before the analyzing the method further comprises:
introducing the reacted liquid solution into a liquid chromatography column to separate compounds in the reacted liquid solution, and
eluting the separated reacted liquid solution to the tandem mass spectrometer for analysis.

* * * * *